US006667618B2

United States Patent
Thesen (10) Patent No.: US 6,667,618 B2
(45) Date of Patent: Dec. 23, 2003

(54) METHOD FOR THE OPERATION OF A MAGNETIC RESONANCE APPARATUS, WHEREBY POSITIONAL CHANGES ARE ACQUIRED WITH ORBITAL NAVIGATOR ECHOS

(75) Inventor: Stefan Thesen, Meckenheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/992,292

(22) Filed: Nov. 16, 2001

(65) Prior Publication Data

US 2002/0130660 A1 Sep. 19, 2002

(30) Foreign Application Priority Data

Nov. 16, 2000 (DE) .......................................... 100 56 874

(51) Int. Cl.[7] ................................................. G01V 3/00
(52) U.S. Cl. ........................................ 324/309; 324/307
(58) Field of Search ............................... 324/307, 309; 600/410

(56) References Cited

U.S. PATENT DOCUMENTS

| | | | | |
|---|---|---|---|---|
| 5,539,312 A | * | 7/1996 | Fu et al. ..................... 324/309 |
| 5,652,516 A | * | 7/1997 | Adalsteinsson et al. ..... 324/309 |
| 5,952,827 A | * | 9/1999 | Feinberg ..................... 324/309 |
| 6,118,273 A | * | 9/2000 | Takizawa et al. ............ 324/309 |
| 6,404,194 B1 | * | 6/2002 | Irarrazabal et al. ......... 324/307 |
| 6,487,435 B2 | * | 11/2002 | Mistretta et al. ............ 600/420 |
| 6,509,735 B2 | * | 1/2003 | Mueller et al. .............. 324/307 |

OTHER PUBLICATIONS

"Human Brain Function," Frackowiak et al., Chapter III, 1997 pp. 43–58.
"Numerical Recipes in C. The Art of Scientific Computing," Press et al, 1992, pp. 408–412.
"Prospective Multiaxial Motion Correction for fMRI," Magnetic Resonance in Medicine, vol. 43, (2000), pp. 459–469.

* cited by examiner

Primary Examiner—Diego Gutierrez
Assistant Examiner—Dixomara Vargas
(74) Attorney, Agent, or Firm—Schiff Hardin & Waite (57) ABSTRACT

In a method for the operation of a magnetic resonance apparatus, wherein a positional change of a region of an examination subject to be imaged relative to an imaging volume of the apparatus is acquired with orbital navigator echos, at least one reference dataset with data points is generated, the data points in the k-space, at least on a partial surface of a spherical surface, being arranged to occupy the partial surface in surface-covering fashion, and the partial surface extending at least around a great circle of the spherical surface corresponding to a maximally expected angular range of the positional change. For acquiring the positional change, a dataset of at least one of the navigator echos is compared to the reference dataset.

30 Claims, 4 Drawing Sheets

FIG 7

METHOD FOR THE OPERATION OF A MAGNETIC RESONANCE APPARATUS, WHEREBY POSITIONAL CHANGES ARE ACQUIRED WITH ORBITAL NAVIGATOR ECHOS

BACKGROUND OF THE INVENTION

1. Field of the Invention

The present invention is directed to a method for the operation of a magnetic resonance apparatus, of the type wherein a positional change of a region of an examination subject to be imaged relative to an imaging volume of the apparatus is acquired with orbital navigator echos.

2. Description of the Prior Art

Magnetic resonance technology is a known technique for acquiring images of the inside of the body of a subject to be examined. In a magnetic resonance apparatus, rapidly switched gradient fields are superimposed on a static basic magnetic field. For triggering magnetic resonance signals, radio-frequency signals are emitted into the examination subject, the magnetic resonance signals that are triggered are being detected, and image data sets and magnetic resonance images being produced on the basis thereof. The magnetic resonance signals are detected by a radio-frequency system, are demodulated in phase-sensitive fashion and converted into complex quantities by sampling and analog-to-digital conversion. These complex quantities are stored as data points in a k-space dataset from which an appertaining image dataset, and thus a magnetic resonance image, can be reconstructed with a multi-dimensional Fourier transformation.

Functional imaging in medicine refers to all methods that utilize a repeated scanning of a structure of organs and tissues in order to image temporally changing processes such as physiological functions or pathological events. In the narrower sense, in magnetic resonance technology functional imaging refers to measuring methods that make it possible to identify and image sensory stimuli and/or areolae in the nervous system stimulated by a motor, sensory or cognitive task, particularly the cerebral areolae of a patient.

The BOLD effect (Blood Oxygen Level Dependent) is the basis of functional magnetic resonance imaging. The BOLD effect is based on different magnetic properties of oxygenated and de-oxygenated hemoglobin in the blood. An intensified neural activity in the brain is assumed to be locally connected with an increased delivery of oxygenated blood, which causes a corresponding intensity boost at a corresponding location in a magnetic resonance image generated with a gradient echo sequence.

In functional magnetic resonance imaging, for example, three-dimensional image datasets of the brain are registered every two through four seconds, for example with an echo planar method. After many image datasets have been registered at various points in time, the image datasets can be subtracted from one another, for example for forming images referred to as activation images, i.e. they can be compared to one another in view of signal differences for the identification of active brain areas. Even the slightest positional change of the brain during the overall exposure time span of the functional magnetic resonance imaging leads to undesirable signal differences that mask the brain activation that is being sought.

In one embodiment of a functional magnetic resonance imaging, image datasets of a region to be imaged are generated with an identical location coding in a time sequence. A retrospective motion correction of the image datasets is implemented following thereupon. Differences between the image datasets that are a result of a positional change of the imaged region with respect to the apparatus during the time sequence thus can be identified and corrected. To that end, a global difference between two image datasets is minimized, with a positional change between the two image datasets, that can be described by motion parameters, being linearized by a Taylor development of the first order, with the assumption of a uniform body motion. The minimization ensues iteratively by the motion parameters being repeatedly estimated with the linearization and applied to one of the two image datasets with interpolations. Such methods are known as Gauss-Newton method in the literature. For a more detailed description, the book by R. S. J. Frackowiak et al., *Human Brain Function*, Academic press, 1996, particularly Chapter 3, pages 43 through 58 is referenced as an example.

In another embodiment of a functional magnetic resonance imaging, a prospective motion correction is implemented during the execution of the functional magnetic resonance imaging. To that end, possible positional changes, i.e. rotations and translation of the region to be imaged, are acquired from image dataset to image dataset by, for example, orbital navigator echos and a location coding is correspondingly adapted during the execution.

An orbital navigator echo is a magnetic resonance signal that is characterized by a circular k-space path and that is generated by a specific navigator sequence. A navigator echo is registered just like a magnetic resonance signal employed for image generation and is correspondingly stored in a navigator echo dataset as complex quantities for data points of k-space that form the circular k-space path. A positional change between the points in time can be determined on the basis of orbital navigator echos that are generated at different points in time. To that end, for example, the navigator sequence is implemented before each generation of an image dataset, a navigator echo is registered, and an appertaining navigator echo dataset is compared to a reference navigator echo dataset for acquiring positional changes.

As is known, a relationship between the image space and k-space exists via a multi-dimensional Fourier transformation. According to the shift theorem of the Fourier transformation, a translation of the region to be imaged in the image space is expressed as a modified phase of complex quantities of data points of k-space. A rotation of the imaged region in the image space effects the same rotation of appertaining data points in k-space. In order to decouple (distinguish) a rotation from a translation in k-space, only amounts of the complex quantities are considered for rotations. A rotation of the imaged region relative to a reference point in time thus can be identified by a comparison of amount values of the navigator echo dataset to those of the reference navigator echo dataset. The phase values are compared for a translation.

For acquiring arbitrary positional changes in three-dimensional space, a respective orbital navigator echo is generated in three planes that are orthogonal to one another. Given positional changes with rotations up to ±8° and translation up to ±8 mm, an imprecision of up to approximately ±1.5° and ±1.5 mm is to be expected for an arbitrary positional change in this contest. Such imprecision can be improved by a repetition of the orbital navigator echos for specifically directed positional changes. After a comparison of a first navigator echo dataset to the reference navigator echo dataset corresponding to an identified positional change, a location coding is adapted for this purpose, and a second navigator echo dataset is registered with the adapted location coding. This dataset in turn is compared to the reference navigator echo dataset, which again leads to the adaptation of the location coding when a positional change is found. Particularly given positional change with a rotational component, however, no improved precision can be achieved in view of the rotational component. The above-discussed use of the orbital navigator echos is explained in greater detail, for example, in the article by H. A. Ward et al., "Prospective Multiaxial Motion Correction for fMRI", Magnetic Resonance in Medicine 43 (2000), pages 459 through 469.

SUMMARY OF THE INVENTION

An object of the invention is to provide an improved method of the type initially described which allows positional changes to be acquired with, among other things, a high precision.

This object is achieved in accordance with the invention in a method for the operation of a magnetic resonance apparatus, which allows a positional change of a region of an examination subject to be imaged relative to an imaging volume of the apparatus to be acquired with orbital navigator echos, wherein at least one reference dataset with data points is generated, with the data points in k-space at least on a partial surface of a spherical surface, being arranged to occupy the partial surface in surface-covering fashion, and wherein the partial surface extends at least around a great circle of the spherical surface corresponding to a maximally expected angular range of the positional change; and wherein for acquiring the positional change, a dataset of at least one of the navigator echos is compared to the reference dataset.

Compared to the above-described method known, wherein only data points are arranged on the spherical surface on three circular paths that are orthogonal relative to one another, the surface-covering occupation of the partial surface with data points achieves clearly improved precision in the acquisition of positional changes. This is particularly true of a portion of a positional change that is to be attributed to a rotation of the region to be imaged.

In an embodiment, the partial surface is equal to the spherical surface. As a result, nearly arbitrary rotations in the broad range from greater than 0° through less than 180° can be acquired with high precision.

In another embodiment, a dataset of a combination of two orbital navigator echos, whose circular k-space paths define two planes that are orthogonal relative to one another, is compared to the reference dataset for acquiring the positional change. Compared to the known method, wherein a combination of three orbital navigator echos that are orthogonal to one another is required, an arbitrary three-dimensional positional change thus can already be acquired with high precision with the combination of only two orbital navigator echos. In applications wherein successive combinations of the aforementioned type are multiply generated for acquiring arbitrary three-dimensional positional changes, a shortening of a pickup duration is achieved compared to the known method. Although the pick-up duration for the reference dataset is lengthened compared to the known method, this is more than compensated by the shortened pickup duration for the combinations of orbital navigator echos with a specific number of combinations.

DESCRIPTION OF THE PREFERRED EMBODIMENTS

Figure 1:
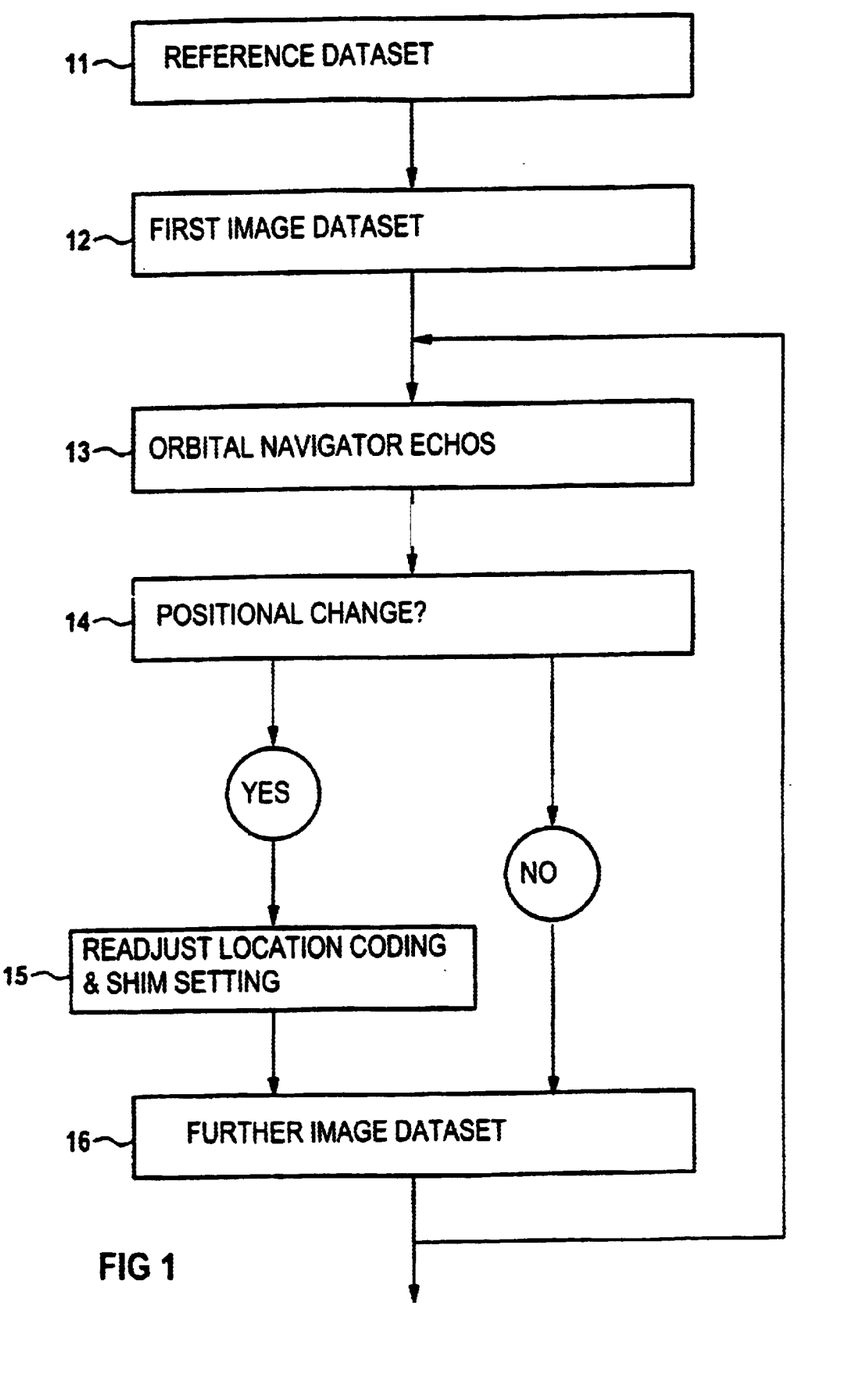
FIG. 1 is a flowchart of a functional magnetic resonance imaging procedure is accordance with the invention.

As an exemplary embodiment of the invention, FIG. 1 shows a flowchart of a functional magnetic resonance imaging procedures with steps 11 through 16. The magnetic resonance apparatus shown schematically in FIG. 2 is referenced as an example for describing the flowchart of FIG. 1.

Figure 2:
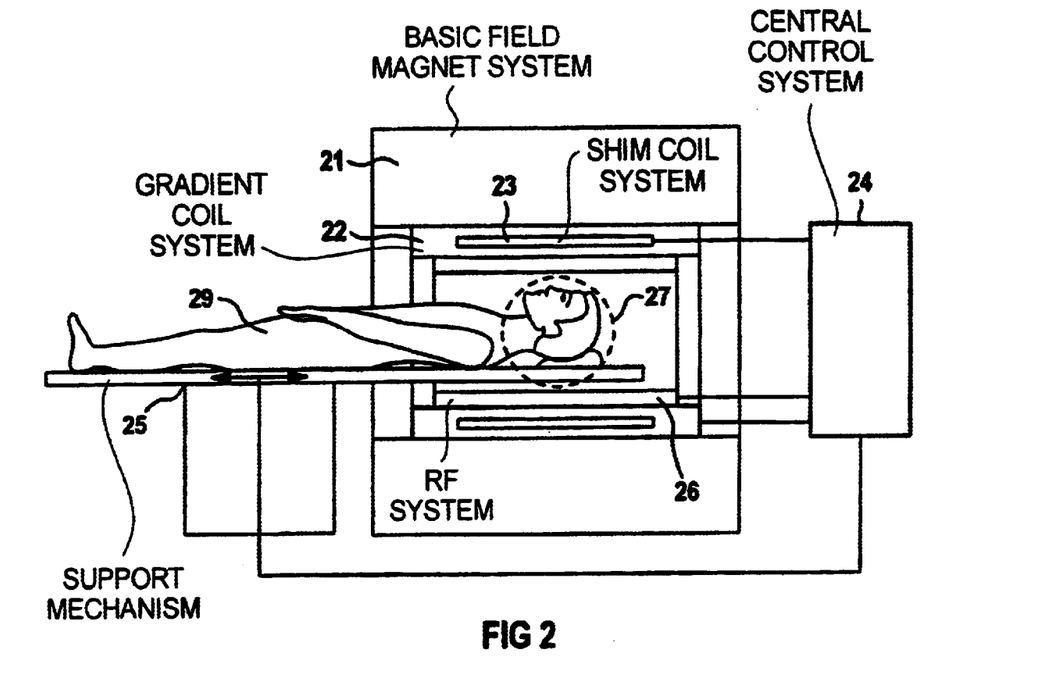
FIG. 2 is a schematic illustration of a magnetic resonance apparatus for executing the inventive method.

The magnetic resonance apparatus of FIG. 2 has a basic field magnet system 21 for generating a basic magnetic field and a gradient coil system 22 for generating gradient fields. A shim coil system 23 is integrated into the gradient coil system 22 for homogenizing the basic magnetic field. For controlling currents in the gradient coil system 22 as well as in the shim coil system 23, both systems 22 and 23 are connected to a central control system 24. Further, the apparatus has a movable support mechanism 25 on which a patient 29 is placed as an examination subject. The apparatus further has a radio-frequency system 26 that, controlled by the central control system 24, emits radio-frequency signals into the patient 29 for triggering magnetic resonance signals and picks up the magnetic resonance signals that are generated.

The central control system 24 is fashioned such that gradient fields generated by the gradient coil system 22 are adjustable possibly in combination with radio-frequency fields generated by the radio-frequency system 26, so that they effect a location coding of the magnetic resonance signals with the examination subject. Further, the central control system 24 is fashioned such that the basic magnetic field in the imaging volume 27 of the apparatus can be homogenized dependent on the examination subject at least partially placed in the imaging volume 27 by setting shim currents of the shim coil system 23 as well as offset currents of the gradient coil system 22. Further, the central control system 24 is correspondingly connected to the bearing mechanism 25 for controlling a displacement of the movable support mechanism 25.

At the beginning of a magnetic resonance examination, the patient 29 is placed on the support mechanism 25 that has been moved as far as possible out of the basic field magnet system 21. For functional magnetic resonance imaging, wherein the head of the patient 29 represents the region to be imaged, the patient 29 is placed head first on the support mechanism 25. Subsequently, the support mechanism 25 is displaced such that the head is positioned in the imaging volume 27 of the apparatus. After the positioning of the head, or simultaneously with the positioning of the head, the offset currents as well as the shim currents are set such that an optimum homogenization of the basic magnetic field is achieved for the head positioned in the imaging volume.

Figure 3:
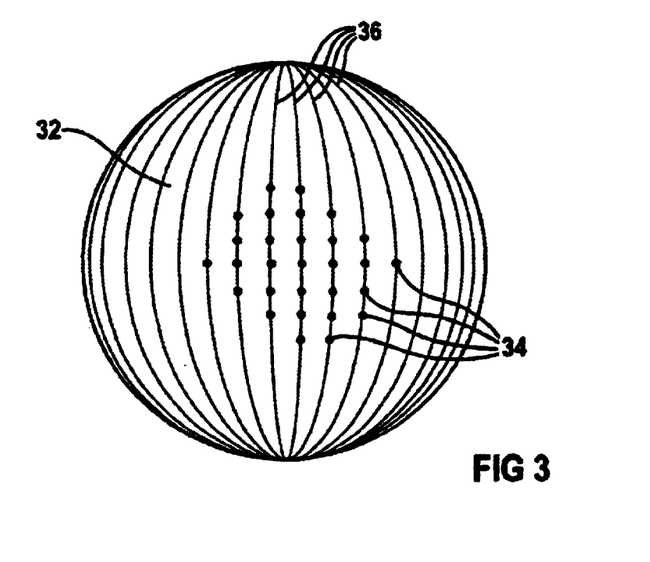
FIG. 3 shows a spherical surface in k-space occupied with data points for a reference dataset in accordance with the invention.

In step 11 of the flowchart of FIG. 1, subsequently, a reference dataset is generated that is employed as the basis for comparison in the functional magnetic resonance imaging for acquiring positional changes of the head relative to the imaging volume 27 from image dataset to image dataset. The reference dataset 34 graphically illustrated in FIG. 3 is formed of data points 34 that are arranged in k-space on a spherical surface 34 occupying k-space surface-covering fashion.

A complex quantity is allocated to each data point 34. For example, the reference dataset is formed by a number of orbital navigator echos, for example 128, whose circular k-space paths 36 are equidistantly distributed on the spherical surface 32 and represent meridians of the spherical surface 32. The sampling points distributed on the meridians form the corresponding data points 34 of the reference dataset. Since the orbital navigator echos are registered with a small flip angle of about 10° and with a short repetition time, a registration duration of less than 20 s can be achieved for the reference dataset. The registration duration of the reference dataset thus remains in an acceptable range.

In a step 12 of the flowchart of FIG. 2, a first image data set of the head of the patient 29 as region to be imaged is registered. The image dataset is thereby generated as three-dimensional image dataset by means of an echo planar method. A fast generation of large three-dimensional image datasets can be implemented with the echo planar method. In other embodiments, similarly fast methods, for example multi-spin echo methods and/or combined gradient echo/spin echo methods can be utilized in addition to the echo planar method, possibly in combination with a half-Fourier technique.

After a prescribable time has elapsed following the registration of the first image dataset and during which the patient 29 executes a cognitive, sensory or motor task, for example a specific movement of a specific finger, a further image dataset of the head is registered in a step 16 of the flowchart of FIG. 1. For identifying the cerebral areolae that participate in the cognitive, sensory or motor task, the two image datasets are essentially subtracted from one another. Even the minutest positional changes of the head between the registration times of the first and of the further image dataset thereby already lead to falsifications. So that said falsifications caused by a positional change of the imaged region do not occur, steps 13 through 15 immediately precede the step 16. To that end, orbital navigator echos are registered in the steps 13 through 15, their navigator echo dataset being compared to the reference dataset for detecting any positional change of the head, and, if a positional change is detected, a location coding and/or a shim setting for the registration of the further image dataset is correspondingly adapted.

To that end, the navigator echo dataset is generated in step 13 of the flowchart of FIG. 1, this being based on the three orbital navigator echos whose circular k-space paths define three mutually orthogonal planes. A complex quantity is allocated to each of the data points of the navigator echo dataset, the data points occupied with complex quantities proceeding from a corresponding sampling of the orbital navigator echos. Any positional change of the head that has occurred is determined in step 14 of the flowchart by comparing the navigator echo dataset to the reference dataset.

The manner by which the navigator echo dataset is compared to the reference dataset for detecting a positional change is explained below as an example. For a clear presentation, an arrangement of planes is first introduced for this purpose, this being composed of three planes that are orthogonal relative to one another and that intersect in a spherical center of the spherical surface 32. Lines of intersection of the arrangement of planes with the spherical surface 32 thereby define a selection dataset on the basis of a corresponding selection of data points 34 of the reference dataset.

For example, one proceeds as follows for determining the part of the positional change to which a rotation of the imaged region can be assigned. That selection dataset that exhibits a maximum coincidence with the navigator echo dataset is sought by means of a step-by-step rotation of the arrangement of planes around the spherical center. A distance function that indicates the maximum coincidence with a value as close as possible to zero serves as the criterion that the maximum coincidence has been achieved. For example, the distance function is formed as a difference between the magnitude values for data points correspondingly arranged in the selection dataset and the navigator echo dataset, and a sum is formed over the differences of all data point pairs.

The start is made with a selection dataset that arises by an alignment of the plane arrangement so that an identical location coding can be allocated to the selection dataset with respect to the navigator echo dataset. When the sum that thereby arises is unequal to zero—zero would mean that no rotation of the region to be imaged occurred between the registration times of the reference dataset and the navigator echo dataset—then a search is made for that navigator echo dataset for which the sum is as close to zero as possible. This ensues, for example, in an iterative method. For defining further selection datasets, the arrangement of planes is rotated by a prescribable step width around the spherical center and the sum that respectively arises is identified. A corresponding interpolation between data points 34 of the reference dataset may be required dependent on the step width of the rotations for forming the respective selection dataset. A rotation of that selection dataset that supplies the resulting sum closest to zero finally determines the rotational component of the sought positional change.

The optimization task described above is solved in a time-efficient way by a method that can be run on a computer system. The Nelder-Mead method, which is also referred to as a downhill simplex method, is referenced as an example, this being described in the book by W.H.Press et al., *Numerical Recipes in C. The art of scientific computing*", Cambridge Univ. Press, 1992, pages 408 through 412, as is the Gauss-Newton method that was initially mentioned.

A translational part of the positional change is finally determined from a corresponding evaluation of phase values for data points of the navigator echo dataset and reference dataset.

When a positional change of the head has occurred, a location coding and/or a shim setting for the further image dataset to be registered in step 16 is correspondingly readjusted in a step 15 of the flowchart of FIG. 1, according to the identified positional change. When, by contrast, no positional change has been found in step 14, then the further image dataset in step 16 is registered with an unmodified location coding and an unmodified shim setting compared to the first image dataset of step 12.

The steps 13 through 16 of the flowchart are repeated suitably often dependent on the requirement of the functional imaging.

Figure 4:
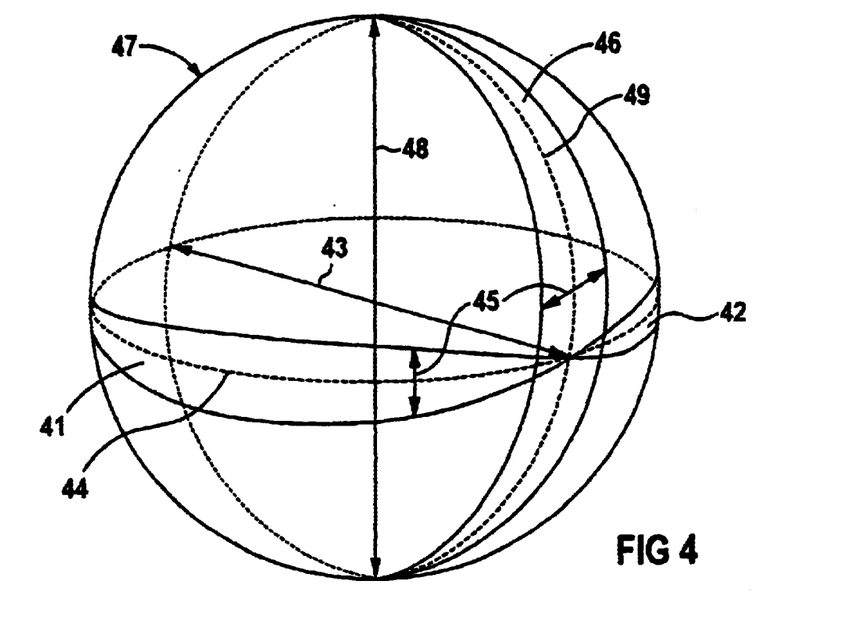
FIG. 4 shows a partial surface occupied with data points for a reference dataset and corresponding to the curved surfaces of spherical cones in k-space in accordance with the invention.
Figure 5:
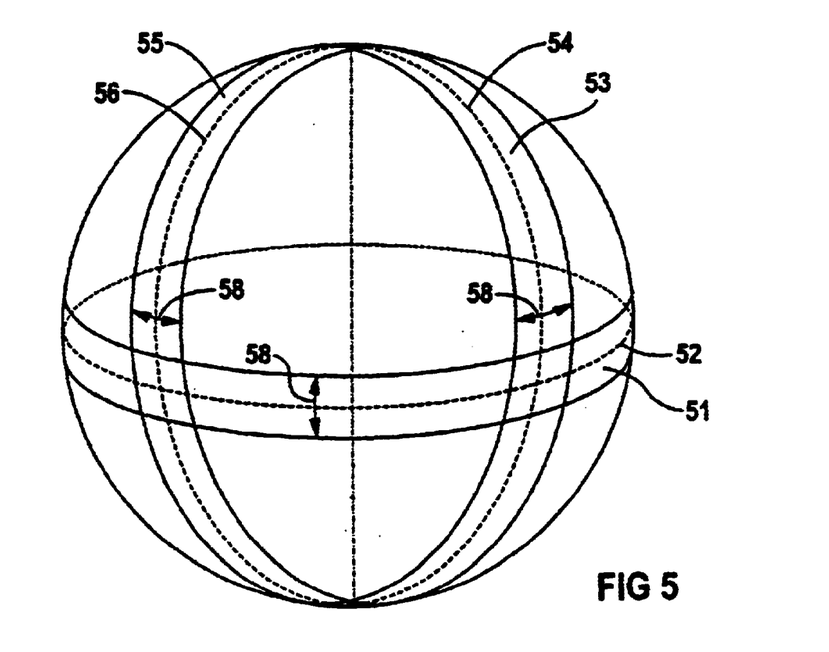
FIG. 5 shows a partial surface occupied with data points for a reference dataset and corresponding to the curved surfaces of spherical segments in k-space in accordance with the invention.

In other embodiments, reference datasets according to FIG. 4 or 5 wherein only a partial surface of the spherical surface 32 is occupied with data points in surface-covering fashion are employed instead of the reference dataset of FIG. 3, whose data points 34 in k-space are arranged on the spherical surface 32 occupying this in surface-covering fashion. Reference datasets whose data points cover a portion of a spherical surface and for which a maximally expected angular range of the positional changes around the planes erected by the orbital navigator echos can be specified, particularly not exceeding ±30°, are advantageously utilized for detecting positional changes. Similar to the reference dataset of FIG. 3, the reference datasets of FIGS. 4 and 5 can be formed by orbital navigator echos. Compared to the reference dataset of FIG. 3, however, a significantly smaller number of orbital navigator echos is needed for a comparable surface density of data points, so that the reference datasets of FIGS. 4 and 5 can be registered faster.

For a reference dataset, FIG. 4 shows a portion of a spherical surface occupied with data points, corresponding to the curved surfaces of a first pair of lunes 41 and 42 and a second pair of lunes 46 and 47. The lunes 41 and 42 have a first, common (shared) diameter 43 with respect to which the lunes 41 and 42 of the first pair are axially symmetrically arranged, and define a great circle 44. The exterior spherical surfaces (segments) of the lunes 41 and 42 are symmetrical to this great circle 44. The lunes 46 and 47 of the second pair likewise have a common diameter 48 with respect to which the lunes 46 and 47 are axially symmetrically arranged and define a great circle 49. The exterior surfaces (segments) of the lunes 46 and 47 are symmetrical to this great circle 49. The lune diameters 43 and 48 as well as the great circles 44 and 49 of the two pairs are aligned at a right angle relative to one another. The great circles 44 and 49 are selected corresponding to the planes defined by two mutually orthogonal orbital navigator echos of a first navigator echo dataset. The lune angle 45 of the lunes 41, 42, 46 and 47 is selected corresponding to a maximally expected angular range of the positional change to be detected.

For a reference dataset, FIG. 5 shows a partial surface of a spherical surface occupied with data points, corresponding to the curved surfaces of three spherical segments 51, 53 and 55. The spherical bands or ribbons 51, 53 and 55 respectively encompass great circles 52, 54 and 56 with respect to which the respective spherical bands 51, 53 and 55 are symmetrical. The great circles 52, 54 and 56 are oriented at right angles relative to one another and are selected, for example, according to the planes defined by three orthogonal navigator echos of a first navigator echo dataset. The thickness 58 of the spherical bands 51, 53 and 55 is selected according to a maximally expected angular range of the positional change to be detected.

Figure 6:
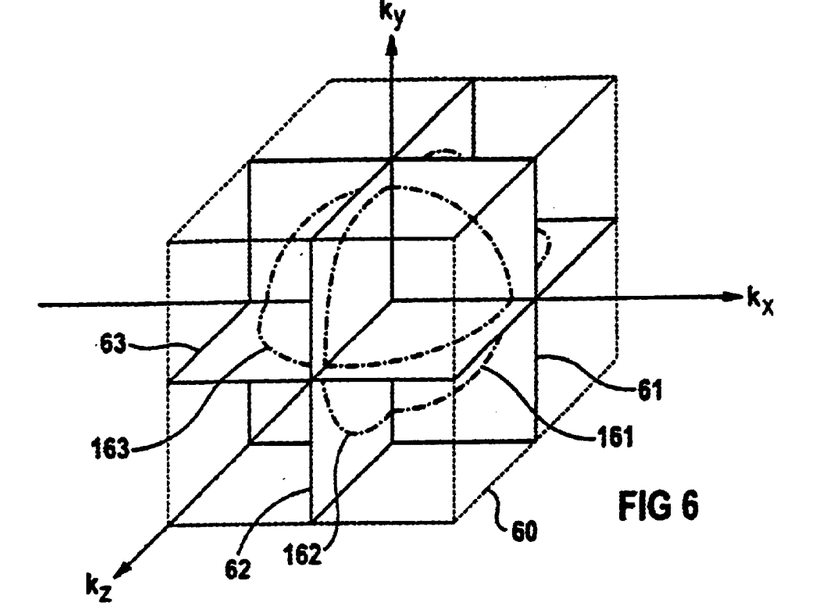
FIG. 6 shows a three-dimensional k-space dataset with three sectional planes orthogonal to one another and defining circular paths for explaining a systematic error in the method of the prior art.
Figure 7:
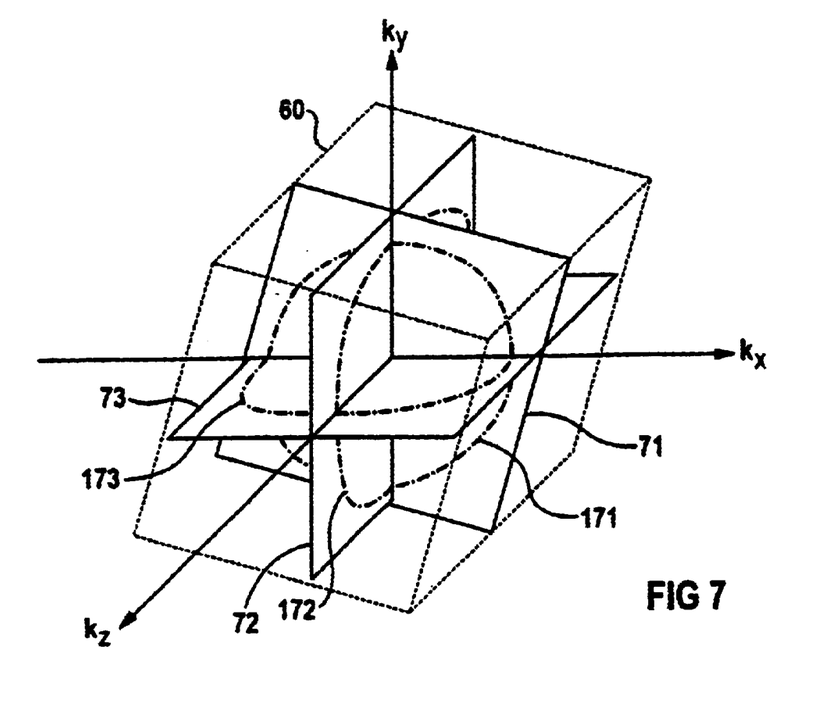
FIG. 7 shows the three-dimensional k-space dataset rotated around an axis compared to FIG. 6, and having three further planes of section orthogonal to one another defining circular paths in the method of the prior art.

On the basis of FIGS. 6 and 7, finally, it is explained why an acquisition of positional changes according to the prior art, wherein navigator echo datasets of three orbital navigator echos that are orthogonal to one another are compared to one another from image dataset to image dataset, fails entirely, or provides only mediocre precision, particularly given positional changes with a rotational part.

According to the prior art, a first navigator echo dataset composed of three orbital navigator echos that are orthogonal to one another is registered for a region to be imaged that is positioned in the imaging volume. For clarity, one can imagine that the first navigator echo dataset arose from a three-dimensional k-space dataset 60 shown in FIG. 6 that reproduces the region to be imaged and that may be assumed to be densely filled matrix-like with data points:

The k-space dataset 60 is arranged in k-space with k-space coordinate axes $k_x$, $k_y$ and $k_z$. The three k-space planes $k_x$–$k_y$, $k_y$–$k_z$ and $k_x$–$k_z$ define three cutting planes 61, 62 and 63 within the k-space dataset 60. A circular path 161, 162 or 163 is placed in the respective cutting planes 61, 62 or 63. The circular paths 161, 162 and 163 thereby have an identical diameter and identical center. The data points situated along the three circular paths 161, 162 and 163 thus form the first navigator echo dataset. The three circular paths 161, 162 and 163 thus represent the three orbital navigator echos. It should be noted again that the derivation of the first navigator echo dataset is only intended to serve for illustration. In practice, the data points are exclusively and directly registered for the first navigator echo dataset without registering a complete k-space dataset 60 that describes the region to be imaged.

A second navigator echo dataset—again composed of three mutually orthogonal orbital navigator echos—is registered after a time lapse during which, for example, the region to be imaged rotates around an axis. The second navigator echo dataset is registered with unmodified location coding compared to the first navigator echo dataset. For clarity, the creation of the second navigator echo dataset is again explained with the assistance of the k-space dataset 60 and FIG. 7.

Due to the rotation of the region to be imaged, the k-space dataset 60 that reproduces the region to be imaged is rotated, for example, around the coordinate axis $k_z$ according to the laws of Fourier transformation. This is correspondingly shown in FIG. 7. The three k-space planes $k_x$–$k_y$, $k_y$–$k_z$ and $k_x$–$k_z$ again define three cutting planes 71, 72 and 73 within the rotated k-space dataset 60. Respective circular paths 171, 172 or 173 again are placed in the cutting planes 71, 72 or 73, the circular paths 171, 172 and 173 again having the same diameter and the same center. The data points situated along the three circular paths 171, 172 and 173 thus form the second alligator echo dataset. The three circular paths 171, 172 and 173 thus correspond to the three orbital navigator echos of the second navigator echo dataset.

For the two navigator echo datasets, this means that only the orbital navigator echos corresponding to the circular paths 161 and 171 with respect to the k-space dataset 60 derive from the same cutting plane 61 or, in this sense, equivalent to the cutting plane 71. In contrast thereto, the orbital navigator echos corresponding to the circular paths 162 and 172 with respect to the k-space dataset 60 derive from two different cutting planes 62 and 72. The same is true of the orbital navigator echos corresponding to the circular paths 163 and 173, which derive from the different planes 63 and 73 with respect to the k-space dataset 60.

According to the prior art, the navigator echos respectively corresponding to the circular paths 161, 162 or 163 are compared to those of the circular paths 171, 172 or 173 for determining a positional change between the registration times of the two navigator echo datasets. For determining a rotational part of the positional change, only the magnitude values are considered for the data points of the navigator echo datasets. Only when comparing the orbital navigator echo corresponding to the circular path 161 to that corresponding to the circular path 171 can it be found that, given a cyclical transposition corresponding to the rotation, the data points of both navigator echos exhibit an identical sequence of amount values from data point to data point. The reason for this is that both the navigator echo corresponding to the circular path 161 as well as the navigator echo corresponding to the circular path 172 derive from the same cutting plane 61 or 71 of the k-space dataset 60.

When comparing data points of the orbital navigator echo corresponding to the circular path 162 to that corresponding to the circular path 172, no simple cyclical transposition of the amount values can be found as a measured quantity for a rotational component because the data points to be compared can exhibit a large variety of magnitude values dependent on the nature of the imaged region as a consequence of their origin from different cutting planes 62 and 72 of the k-space dataset. This applies as well to a comparison of data points of the orbital navigator echo corresponding to the circular path 163 to those corresponding to the circular path 173.

When a positional change with a rotation around more than one axis occurs, then the determination of a rotational part fails in all three orbital navigator echos. It is only within comparatively small rotations that magnitude values identically arranged within the navigator echo datasets do not change so greatly that the method according to the prior art does not fail completely. However, only the mediocre precision initially set forth is thereby achieved. It is also clear on the basis of the foregoing that no improved precision can be achieved for the rotational components to be identified given the initially described, repeated registration of a second navigator echo dataset, because the above-described, systematic error arising in the comparing steps according to the prior art is not avoided. This systematic error does not appear in the inventive method.

The above discussion with reference to the example of functional magnetic resonance imaging can be correspondingly transferred to diffusion and perfusion imaging as well as to normal magnetic resonance imaging wherein a magnetic resonance image is, in particular, not registered with a single sequence pass.

The inventive method can be unproblematically utilized in diffusion imaging since the diffusion coding is implemented following the orbital navigator echos or, respectively, the generation of the reference dataset, so that a mutual deterioration of detecting positional change and diffusion coding can be precluded.

In normal magnetic resonance imaging, for example with a turbo spin echo method based on a multi-slice technique, whereby a three-dimensional image dataset is built up slice by slice, positional changes of the imaged region from slice registration to slice registration can be detected and correspondingly corrected according to the inventive method. In another embodiment, the registration of a two-dimensional slice can also be interrupted once or repeatedly in order to detect positional changes that have potentially occurred with the inventive method. This is also true for volume techniques.

In perfusion imaging, it is particularly advantageous to select a comparatively large diameter for the orbital navigator echos as well as the reference dataset with respect to the region to be imaged, so that a contrast agent administration that mainly produces contrast changes in center-proximate areas of the region to be imaged does not have a vitiating effect on the detection of positional changes.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for operating a magnetic resonance apparatus comprising the steps of:
    positioning an examination subject in an imaging volume of a magnetic resonance apparatus, said subject being subject to a positional change in said imaging volume;
    obtaining a reference dataset from said examination subject containing data points in k-space situated on at least a portion of a spherical surface, said data points occupying said portion of said spherical surface by covering an area of said spherical surface, and said portion of said spherical surface extending at least around a great circle of said spherical surface corresponding to a maximally expected angular range of said positional change;
    generating a plurality of orbital navigator echoes and obtaining a plurality of data sets from said examination subject respectively associated with said orbital navigator echoes; and
    identifying said positional change by comparing a dataset associated with at least one of said orbital navigator echoes to said reference dataset.

2. A method as claimed in claim 1 comprising selecting said great circle to correspond to a circular k-space path formed by data points in the dataset associated with one of said orbital navigator echoes.

3. A method as claimed in claim 1 wherein said spherical surface defines a sphere, and comprising the step of defining said portion of said spherical surface by respective exterior surfaces of at least two pairs of lunes of said sphere, the lunes in each pair having a common lune diameter with respect to which the lunes in the pair are axially symmetrical, with the respective exterior surfaces of the lunes in each pair proceeding along a great circle of said spherical surface, and wherein the respective diameters of the pairs of lunes and the respective great circles of the pairs of lunes are orthogonal.

4. A method as claimed in claim 3 wherein said portion of said surfaces formed by respective exterior surfaces of three pairs of lunes of said sphere.

5. A method as claimed in claim 3 wherein each of said lunes has a lune angle in a range between approximately 5/ through approximately 60/.

6. A method as claimed in claim 1 comprising defining said portion of said spherical surface as respective curved surfaces of at least two spherical segments, each of said spherical segments being symmetrically disposed on a great circle of said spherical surface, with the respective great circles relative to which the spherical segments are symmetrical being orthogonal.

7. A method as claimed in claim 6 wherein said portion of said surface comprises respective curved surfaces of three spherical segments.

8. A method as claimed in claim 6 wherein each spherical segment has a thickness in a range between approximately 5% through approximately 30% of a diameter of said spherical surface.

9. A method as claimed in claim 1 wherein said portion of said spherical surface equals said spherical surface.

10. A method as claimed in claim 1 wherein the orbital navigator echoes have respective circular k-space paths of identical diameters.

11. A method as claimed in claim 1 comprising obtaining said reference dataset before generating said orbital navigator echoes.

12. A method as claimed in claim 1 comprising, for detecting said positional change, forming a combination dataset as a combination of the respective datasets of two of said orbital navigator echoes having respective circular k-space paths in two planes that are orthogonal to each other, and comparing said combination dataset to said reference dataset.

13. A method as claimed in claim 1 comprising, for detecting said positional change, forming a combination dataset as a combination of the respective datasets of three of said orbital navigator echoes having respective circular k-space paths in three planes that are orthogonal to each other, and comparing said combination dataset to said reference dataset.

14. A method as claimed in claim 1 wherein the step of comparing the dataset associated with at least one of said orbital navigator echoes to said reference dataset comprises forming at least one circular path on said portion of said spherical surface, from respective values of the data points of said reference dataset, most closely coinciding with a correspondingly formed sequence of values for the dataset associated with said at least one of said orbital navigator echoes, and identifying said positional change from said at least one circular path.

15. A method as claimed in claim 14 comprising forming said at least one circular path by interpolating said values of the data points of the reference dataset.

16. A method as claimed in claim 14 wherein said data points of said reference dataset are complex quantities, and comprising using the respective magnitudes of said complex quantities as said values for forming said at least one circular path.

17. A method as claimed in claim 14 wherein said circular path has a distance function relative to said sequence of values for said dataset of said at least one of said orbital navigator echoes, and wherein the step of forming said at least one circular path includes minimizing said distance function using a multi-dimensional minimization method.

18. A method as claimed in claim 17 comprising using a Nelder-Mead method as said multi-dimensional minimization method.

19. A method as claimed in claim 17 comprising using a Gauss-Newton method as said multi-dimensional minimization method.

20. A method as claimed in claim 1 comprising generating said reference dataset using a gradient echo method with a flip angle of about 10° and a repetition time of or less than about 0.156 seconds.

21. A method as claimed in claim 1 comprising generating said orbital navigator echoes using a gradient echo method with a flip angle of about 10° and a repetition time of or less than about 0.156 seconds.

22. A method as claimed in claim 1 comprising generating said reference dataset and said orbital navigator echoes using a gradient echo method with a small flip angle of about 10° and a repetition time of or less than about 0.156 seconds.

23. A method for operating a magnetic resonance apparatus comprising the steps of:

positioning an examination subject in an imaging volume of a magnetic resonance apparatus, said subject being subject to a positional change in said imaging volume and containing a region to be imaged;

obtaining a reference dataset from said examination subject containing data points in k-space situated on at least a portion of a spherical surface, said data points occupying said portion of said spherical surface in surface-covering fashion, and said portion of said spherical surface extending at least around a great circle of said spherical surface corresponding to a maximally expected angular range of said positional change;

generating a first image dataset, with location coding, of said region;

generating a plurality of orbital navigator echoes and obtaining a plurality of data sets from said examination subject respectively associated with said orbital navigator echoes;

identifying said positional change by comparing a dataset associated with at least one of said orbital navigator echoes to said reference dataset;

adjusting said location coding dependent on said positional change; and generating at least one further image dataset of said region with the adjusted location coding.

24. A method as claimed in claim 23 comprising generating all of said datasets using a static basic magnetic field, and comprising the additional steps of actively shimming said static basic magnetic field with a shim coil system having shim coil currents flowing therein, and adjusting said shim coil currents dependent on said positional change.

25. A method as claimed in claim 23 comprising obtaining all of said datasets using a gradient coil system having offset currents flowing therein, and comprising the additional step of setting said offset currents dependent on said positional change.

26. A method as claimed in claim 23 comprising generating all of said datasets using a static basic magnetic field and a gradient coil system, said gradient coil system having offset currents flowing therein, and comprising the additional steps of actively shimming said static basic magnetic field with a shim coil system having shim coil currents flowing therein, and adjusting said shim coil currents and setting said offset currents dependent on said positional change.

27. A method as claimed in claim 23 comprising generating at least one of said first image dataset and said further image dataset as a three-dimensional image dataset using an echo planar method.

28. A method as claimed in claim 23 comprising generating said reference dataset using a gradient echo method with a small flip angle and a short repetition time.

29. A method as claimed in claim 23 comprising generating said orbital navigator echoes using a gradient echo method with a flip angle of about 10° and a repetition time of or less than about 0.156 seconds.

30. A method as claimed in claim 23 comprising generating said reference dataset and said orbital navigator echoes using a gradient echo method with a small flip angle of about 10° and a repetition time of or less than about 0.156 seconds.

* * * * *